(12) United States Patent
Dufait et al.

(10) Patent No.: US 6,915,696 B2
(45) Date of Patent: Jul. 12, 2005

(54) INTERSECTING ULTRASONIC TRANSDUCER ARRAYS

(75) Inventors: Rémi Dufait, Tours (FR); An Nguyen-Dinh, Valleres (FR); Philippe Auclair, Tours (FR); Christophe Notard, La Croix en Touraine (FR); Aimé Flesch, Andrésy (FR)

(73) Assignee: Vermon, Tours Cedex (FR)

( * ) Notice: Subject to any disclaimer, the term of this patent is extended or adjusted under 35 U.S.C. 154(b) by 0 days.

(21) Appl. No.: 10/373,840

(22) Filed: Feb. 27, 2003

(65) Prior Publication Data

US 2004/0168517 A1 Sep. 2, 2004

(51) Int. Cl.[7] ............................................... G01N 29/24
(52) U.S. Cl. .......................... 73/626; 310/336; 600/459
(58) Field of Search .................. 73/625, 626; 310/334, 310/336; 600/459

(56) References Cited

U.S. PATENT DOCUMENTS

| | | | |
|---|---|---|---|
| 3,881,164 A | 4/1975 | Kossoff | |
| 4,570,488 A | 2/1986 | Miwa et al. | |
| 4,671,293 A | 6/1987 | Shaulov | |
| 4,870,867 A | 10/1989 | Shaulov | |
| 5,103,129 A | * 4/1992 | Slayton et al. | 310/334 |

* cited by examiner

Primary Examiner—John E. Chapman
(74) Attorney, Agent, or Firm—Stites & Harbison PLLC; Ross F. Hunt, Jr.

(57) ABSTRACT

A method is provided for manufacturing crossing/intersecting transducer arrays including first and second ultrasonic transducer arrays which intersect centrally of one another. Each transducer operates independently without any decrease in acoustic performance. The first and second arrays have their own independent signal electrodes, respectively disposed on the front and rear surfaces of the device. Because the arrays are built on a unique piezoelectric member, a portion of signal electrode of each array is adapted to be connected to ground in a manner permitting proper operation of the entire array. A method of forming matching layer sets incorporating electrical interconnections is also provided.

8 Claims, 6 Drawing Sheets

INTERSECTING ULTRASONIC TRANSDUCER ARRAYS

BACKGROUND OF THE INVENTION

1. Field of the Invention

The present invention relates to ultrasonic transducer arrays and, more particularly, to intersecting transducer arrays and methods for making the same.

2. Related Art

In a preferred embodiment of the invention discussed below, a biplane phased array transducer device is provided for applications such as medical imaging and/or treatment (therapy) and, more particularly, for use in endocavity ultrasonic imaging probes for trans-rectal and trans-vaginal applications where multisectional views of the examined organ are often desired for diagnosis enhancement.

Currently, there is a large number of different ultrasonic probes designed for many different specific applications, clinical needs and other requirements. Biplane array transducers are representative of a particular group of ultrasonic probes that is especially suitable for use under certain conditions, i.e., where only limited manipulation or movement of the probe is possible. Such probes are, therefore, generally equipped with two separate array transducers disposed in such a manner that the scanning planes thereof intersect in the field of view. This has obvious advantages because the organ being examined is simultaneously separated in two different orientations.

A very early, if not the first, biplane transducer device for imaging applications was disclosed in U.S. Pat. No. 3,881,164 to Kossoff, wherein an apparatus for ultrasonic examination comprising first and second intersecting arrays is described. In this patent, one of the arrays is constructed as the primary transducer whereas the other array is disposed perpendicularly thereon and is complementary to the primary array. The complementary array is interrupted by the passage of the primary array therethrough, and no manufacturing method for the apparatus is disclosed in the patent.

In U.S. Pat. No. 4,570,488 to Miwa et al, there is proposed a method for observing two distinct sections of the object of examination simultaneously, using two perpendicular transducers operated at the same time. In one preferred embodiment, both of the arrays are constructed such that the signal and ground electrodes are formed on the same surface of the piezoelectric member. The intersecting arrays possess an overlapping area which is defined in the elevational dimension of the arrays. Because the signal electrodes cross each other, the overlapping area is of a matrix shape. This matrix area is composed of hundreds of individual small surface elements. Although the design of this transducer array appears to be quite simple, providing electrical interconnections in the matrix area is a difficult task with respect to both device construction and system upgrade because each element in the overlapping area must be addressed.

Another biplane transducer array combining perpendicularly intersecting array electrodes is that disclosed in U.S. Pat. Nos. 4,671,293 and 4,870,867, both to Shaulov. In the '293 patent, a rectangular biplane phased array is described which uses a 1–3 piezoelectric composite as the active component. The major surfaces of the piezoelectric member are plated to form signal electrodes. Thereafter, dicing is performed through the electrodes, and partially into the piezoelectric composite member, to form patterns of perpendicularly oriented electrodes. The electrodes are successively connected to the excitation signal and ground of the system to provide biplane operation of the transducer. The '293 patent discloses that partial dicing (dicing to a depth of 25–90% of the total thickness) in the piezoelectric material is compulsory for achieving acceptable transducer performance. The '867 patent relates to a variation wherein the transducing device is still built with intersecting portions but including protruding branches. Electrode patterns are simultaneously disposed on the top and bottom surfaces of each branch of the transducer to form transducer arrays of an intersected shape. Because the arrays have their electrodes laminated on the opposite surface of the piezoelectric member, no matrix section of electrodes is formed as in the prior art. However, the patent relates only to driving of the transducer array and to the method of dicing the elements of the transducer array, and does not disclose a solution to the problem of, nor a method for, manufacturing the array.

Conventionally, ultrasonic devices are designed based on one or more electrode plated piezoelectric members having a first surface facing the examination medium and a second surface loaded with an attenuating backing member. When the transducer is electrically excited, ultrasonic energy is emitted from both of the opposite surfaces of the piezoelectric member, although only the energy from the front face of transducer is of benefit with respect to producing the desired scanning images. The acoustic energy emitted from the rear surface of the piezoelectric member is cancelled by attenuation or backscattering in the backing member so as to avoid artifacts. In order to enhance the energy transmission coefficient along the front path, the transducer is commonly equipped with a front impedance matching device or impedance matching layers which also perform frequency accentuation filter functions to provide broadening of the bandwidth of the transducer device. As long as the ultrasonic transducer employs heavy acoustic impedance piezoelectric materials (ceramics, composites, single crystals and the like) for producing the ultrasounds, such front path matching layers are required to provide acceptable performance with respect to imaging biologic tissues.

In conventional constructions, as well known in the art, the transducer array is commonly composed of a plurality of diced piezoelectric elements which are maintained in place by means of the backing member disposed on the rear face of the piezoelectric member. An individual acoustic matching device is provided on the front surface of every piezoelectric element, and kerfs (void spaces) between the piezoelectric elements are usually filled with flexible resin to physically isolate one piezoelectric element with respect to its neighbors. The rear electrode of the transducer array is connected to a flexible (flex) printed circuit which connects elements of the transducer array to coaxial cables, optionally via intermediate connectors. In general, the front electrodes of transducer are all shunted together and then connected to the system zero potential. Optionally, an independent overall shield is advantageously provided over the external surface of the transducer device to improve EMI immunity. As long as the array transducer is shaped in 1D configuration, providing a connection to ground in this way is quite convenient and is well suited to both linear and curved linear arrays.

With regard to the intersecting transducer arrays as disclosed in some of the prior art, the transducer comprises at least two intersecting arrays which overlap in the central area of the device. In order to enable each separate array to operate properly, the central area comprises portions of electrodes disposed such that the elemental electrodes or elements can be respectively obtained for the two arrays. To achieve such an electrode mapping, the central electrode is split into regular portions forming a matrix of electrodes (as in U.S. Pat. No. 4,570,488 described above) wherein each element is independently addressed. A multiplexing device is thus required to ensure that the proper elements of the array are addressed in the appropriate sequence during operation. Control of such a multiplexing operation is complex and an appropriate multiplexing device could be more complex to manufacture than a matrix array itself.

Another limiting aspect of an intersecting transducer array construction concerns the acoustic behavior of such a transducer array. It has been widely reported in the literature that several spurious vibration modes occur strongly when the transducer is excited. One of the most common and probably the most important of the spurious modes is created by Lamb (or plate) effects that result from local vibrations of the piezoelectric member. Several species of Lamb waves may simultaneously exist but all differ in velocity and polarization. In general, the lowest order modes of Lamb waves are transversely polarized and propagate along the wave guide (transducer member). The propagation velocity of such modes is governed by the elastic and shear properties of the piezoelectric material. As a result, in a sheet material of limited thickness, such as the piezoelectric member of the transducer or the matching layers, the velocity of Lamb wave may be higher than the compressional sound velocity, thereby favoring the transmission of unwanted acoustic energy in the direction of the interrogation, with a deviation angle corresponding to the ratio between the Lamb wave velocity and the longitudinal velocity in the medium. This spurious acoustic radiation dramatically restricts the angular response of the transducer so that as a result, artifacts can be observed in the resultant images.

In order to combat the effects of Lamb wave propagation, nonhomogeneous inclusions or barriers have been provided in the support member which produce strong attenuation or backscattering of the transverse wave propagation so as to improve the quality of the array performance. One of the most common and efficient methods used here is to cut through or into the material forming the member and then fill the resultant void spaces with a flexible resin or particle filled polymer to provide a physical barrier against coupling waves. Currently, such a through cut method is widely used in PZT D1 array transducer fabrication. Once the transducer is assembled, a dicing operation is performed at least through the piezoelectric thickness to produce individual transducer elements spaced from each other. Optionally, grooving of the backing member can also be provided in a manner to attenuate mass/spring modes that particularly affect phased array constructions. Unfortunately, with respect to an intersecting array construction such as disclosed in the prior art discussed above, the through cutting techniques previously described are impractical for use in manufacturing of such an array because of the particular arrangement of the two intersected arrays.

Because of the problems discussed above, conventional biplane devices having an intersecting configuration are commonly made using a partial cut method so as to preserve the transducer by avoiding a complete separation of the array elements. Further, no crossed shape intersecting array configuration is fully disclosed in the prior art because of the task of connecting all of the elements of the intersecting arrays.

With regard to a suitable method for manufacturing intersecting arrays, even if a through cut operation combined with resin filling of the resultant kerfs might appear to be an ideal solution in certain configurations (i.e., a 1D array) for avoiding Lamb wave propagation, such an approach using a partial cut into the piezoelectric member will not yield a proportional effect on the Lamb modes. In this regard, partial cuts into the piezoelectric member will result in the creation of two sub-structures, one formed by the portion of the member defined by the thickness of the grooves and the other comprising the remaining portion of the member. Each sub-structure can be considered to be a "new" or different member and, therefore, the initial problem is increased because of the combined spurious wave resulting from the two sub-structures. As a result, if the piezoelectric member cannot be through cut and filled with an attenuating material, the best way for making a reliable and efficient transducer imaging device might be to use a 1–3 composite piezoelectric wherein the material structure already comprises vertical thin pillars embedded in a resin matrix. Such ceramic pillars will offer natural obstacles to Lamb wave propagation thereby making the composite an efficient base material for an uncut transducer.

Another factor that significantly limits the use of current biplane array transducers is the need to use dedicated or upgraded hardware to effect the required transducer switching. In this regard, imaging systems are conventionally designed for operation in conjunction with a 1D scanning probe which employs a linear transducer arrangement. The transducers of this arrangement are disposed along the major axis thereof (azimuth) to provide electronic beam forming and focusing. Each probe is electronically coded and is automatically identified by the system when plugged in, and a corresponding beam forming program is then uploaded. The scanning image is displayed as a 2D (planar) representation wherein the vertical dimension represents the penetration of the image while the lateral dimension corresponds to the transducer azimuth geometry associated with the system steering amplitude. Thus, using a biplane array transducer with a 1D conventional imaging system will result in incompatibility and consequently, in incorrectly displayed images.

In order to permit the use of biplane array transducers in conventional imaging systems, some basic conditions must be fulfilled. For example, the existing system is provided with at least two probe connectors wherein the first array of the probe is plugged in to the first connector while the second (intersected) array of the probe is connected to the second connector of the system. With this arrangement, users simply have to select, on the system interface, either the first connector or the second connector in order to provide the desired operation. Both arrays are expected to be identified by the system as known thereto.

Given the aforementioned shortcomings with respect to combating Lamb wave effects and the lack of compatibility of biplane ultrasonic transducers with existing imaging systems, there is obviously a need for both an improvement in transducer performance and with respect to the incorporation of switching features between the crossing arrays of the transducer in order to make the use thereof transparent to the system and to users of the system.

SUMMARY OF THE INVENTION

A principal object of the present invention is to provide an intersecting phased array transducer device which incorporates means for providing Lamb wave reduction in the transducer core as well as a switching device disposed in the vicinity of the transducer module for providing the device with a unique and restricted number of pin connectors. Such a device is achievable through the provision of interconnect means specifically designed for the intersecting area of electrodes characteristic of such devices. Further, a transducer device according to a preferred embodiment of the invention additionally exhibits an enhanced degree of flexibility thereby allowing curving or bending of the surface of the transducer device after the device is complete.

According to one principal aspect of the invention, there is provided an intersecting ultrasonic array transducer which is suitable for imaging applications, and, more particularly, a curved intersecting array transducer device that can be used as biplane transducer. In accordance with a related aspect of the invention, methods are provided for making such ultrasonic array transducer devices.

According to a further important aspect of the invention there are provided an improved matching layer device and methods for making the same.

Further features and advantages of the present invention will be set forth in, or apparent from, the detailed description of preferred embodiments thereof which follows.

DESCRIPTION OF THE PREFERRED EMBODIMENTS

Figure 1:
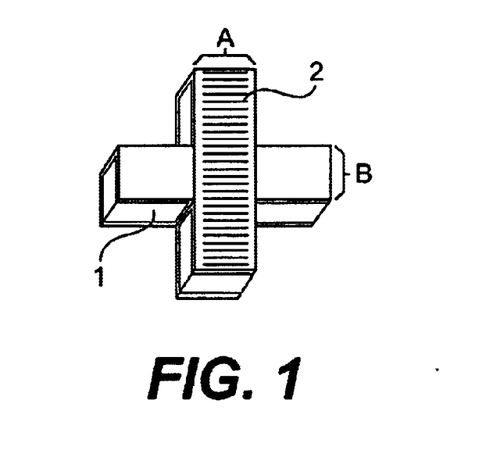
FIGS. 1 is a perspective view of intersecting an ultrasonic array transducer device in accordance with a preferred embodiment of the invention, showing the basic device without associated matching layers, backing layer and interconnection means.

As illustrated in FIG. 1, a transducer in accordance with the invention preferably includes a vibrating piezoelectric member 1 that is of an ordinary cross shape. Piezoelectric member 1 is preferably made from a ceramic-polymer based composite material and, preferably, both branches are made from the same composite member. The piezoelectric member 1 also comprises electrodes or an electrode pattern 2 and 3 on the top and bottom major surfaces thereof disposed in a manner such as to create an electrical field, when an excitation voltage is applied thereto of a strength such as to cause vibration of the piezoelectric member 1 and thus produce ultrasound energy.

As illustrated, the transducer device is actually composed of branched sub-sections or branches A and B which are shown as intersecting perpendicularly to one another, for simplicity of explanation and understanding. Further, in the illustrated embodiment, the sub-sections A and B intersect symmetrically and are of a flat shape as shown in FIGS. 1 and 2.

Figure 2:
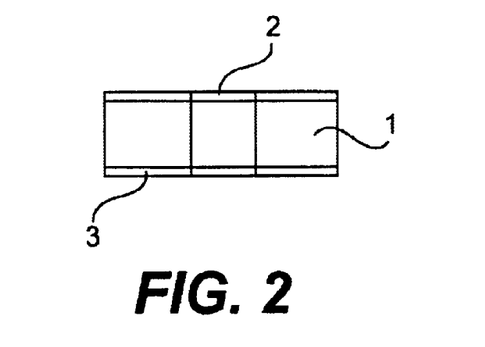
FIG. 2 is a side elevational view of the device of FIG. 1.

A side elevational view of the transducer is shown in FIG. 2 wherein the piezoelectric member 1 is shown as being sandwiched between opposing electrode patterns 2 and 3. Again, for the sake of simplicity, the two sub-sections of a transducer have the same thickness and are formed to have a common surface. Of course, the thickness of sub-sections A and B may be different if desired. According to the preferred embodiment of the invention illustrated in the drawing, at least two branched sub-sections or branches (A and B) form the intersecting array transducer, although more than two sub-sections can be employed.

Figure 3:
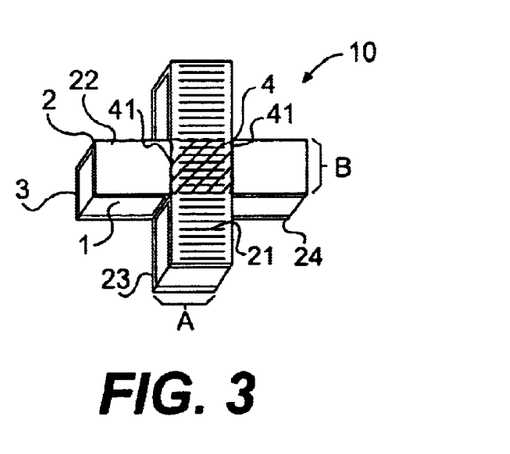
FIG. 3 is a view similar to FIG. 1 showing further details of the device.

Referring to FIG. 3, in the embodiment of the invention depicted therein of a perpendicular intersecting array transducer device, the device comprises at least a first sub-section A disposed vertically and a second sub-section B disposed horizontally. The top surface of the transducer is the emitting face, meaning that, as explained above, the opposing face must be provided with, i.e., loaded with, a backing member or attenuator to eliminate reverberation echoes being emitted from the rear face of the transducer. Preferably, sub-sections A and B are of the same dimension and acoustic specifications so they are able to provide the same images, and, further, can be connected to the same system beam former.

As shown in FIG. 3, the branched sub-section or branch A, herein illustrated as extending vertically, is composed of a piezoelectric member 1 having the front face thereof covered by a signal electrode 21 and the rear face thereof covered by a ground electrode 23. Electrodes 21 and 23 entirely cover the main surfaces of the piezoelectric member 1, and should be preferably constructed as perfectly opposing parts in a manner such as to optimize the electrical field of the transducer. The perpendicular branched sub-section or branch B is inherently horizontally disposed, and therefore, includes a common area of intersection or intersected area 4 that is shared with the branch A. Branch B also comprises a ground electrode 22 and a signal electrode 24. It is noted that the ground and signal electrode patterns of branches A and B are the reverse of each other on the transducer so as to avoid the formation of a central crossing area with a very large number of electrode elements.

In the preferred embodiment being considered, preference is given to the signal electrode patterns 21 and 24, which are entire, or unbroken, for the interconnection stage. In this regard, the electrode elements of each branch extends over the full length of the respective branch, so that, as a consequence, the ground electrodes 22 and 23 of the branches A and B are interrupted at the boundaries of the common area or portion 4 without electrically shunting the signal electrode patterns 21 and 24.

Figure 4A:
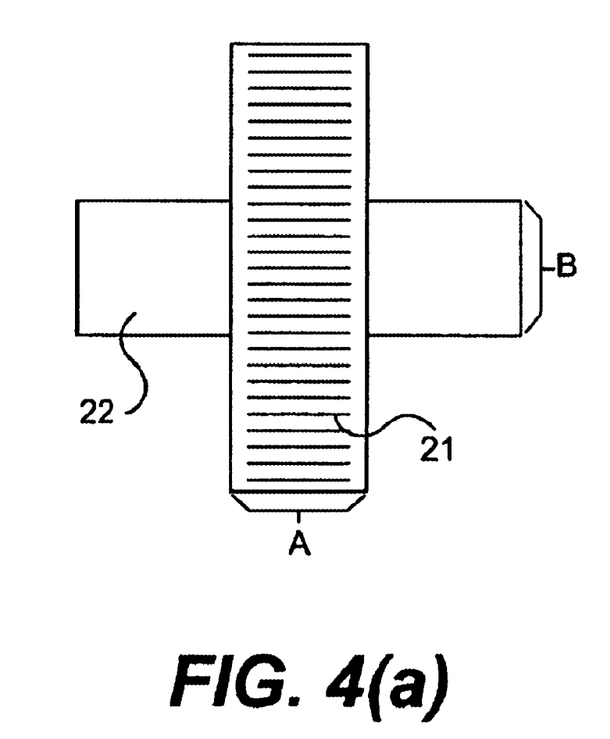
FIGS. 4(a) and 4(b) are a top plan view and a bottom plan view, respectively, of the device of FIG. 1.
Figure 4B:
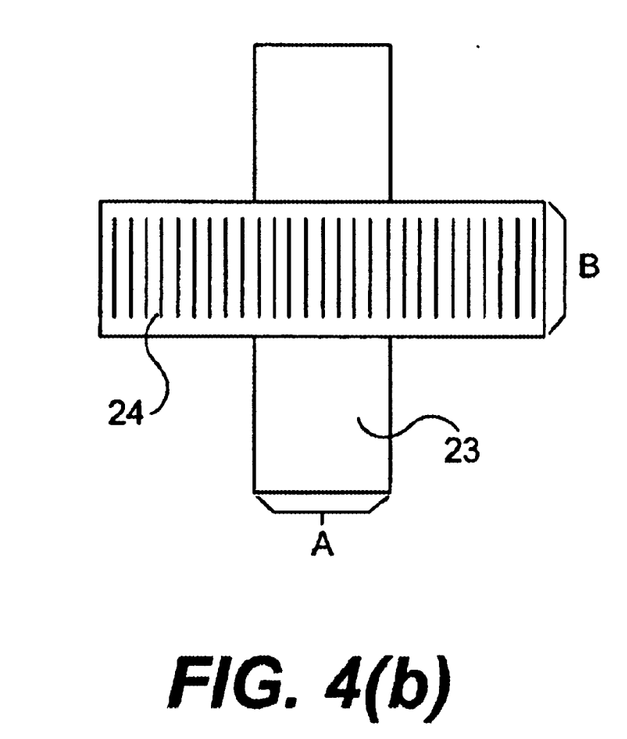

In FIGS. 4(a) and (b), front and rear faces of the transducer are shown, and thus FIGS. 4(a) and (b) clearly depict the manner in which the signal electrodes 21 and 24 have to be arranged on the surface of the transducer in order to achieve an operational intersecting transducer array device. In this regard, the front face or top plan view of FIG. 4(a) shows vertical branch A with its signal electrode 21 as well as branch B formed by the two perpendicular portions or branches which are covered by the uncut ground electrode 22, while the rear face or bottom plan view of FIG. 4(b) illustrates the same branches A and B with their corresponding electrode pattern of signal electrode 24 and ground electrode 23.

Referring again to FIG. 3, which, as indicated above, is a perspective view of the intersecting array device, the piezoelectric member 1 is of a cross shape produced by a milling or punching operation performed on a plate of the base piezoelectric composite. The piezoelectric member is then electrode plated on the opposite main surfaces thereof. Metals selected from the group of ductile metals (copper, gold, silver, nickel and the like) are well suited for this purpose. Metallization of the electrodes can be carried out using chemical or mechanical techniques with no impact on the basic manufacturing process for the transducer. Preferably, physical, i.e., mechanical as opposed to chemical, deposition of nickel/gold is recommended in order to improve the adherence of the electrodes and to provide sufficient electrical conductivity as well. Copper can also be used advantageously as the electrode material because of its very good conductivity/cost ratio. In the case of the use of copper electrodes, a chemical deposition method is preferred.

Once the electrodes are deposited on the main surface of the piezoelectric member 1, a polarization operation can be performed to optimize the piezoelectric behavior of the material. In this regard, a voltage of 1500V/cm can be applied to the faces of the composite to achieve maximum polarization of the piezoelectric member 1. This operation should preferably be performed in a dielectric liquid bath to avoid any electrical arcing that might otherwise destroy the piezoelectric material.

In the next step, the patterning of the front electrode is then carried out. The preferred method for obtaining electrode etching as required by the intersecting transducer device is an ion beam etching method wherein an insulation mask is deposited on the surface of electrode and ion etching is then performed through the mask. A PCB chemical etching technique is also suitable, although with less precision as to the definition of the elemental electrodes or elements. Because such etching methods are common practice in electronic manufacturing, no further details or specific illustration of particular embodiments thereof will be provided.

At the completion of the etching operation, and referring again to FIG. 3, the front surface of the transducer 10 will have disposed thereon a first portion of the signal electrode 21 whereat there are arranged elementary signal electrodes of the branch or sub-section A, as well as two portions of ground electrode 22 belonging to branch B. The latter are separated by the central "intersected" area 4 and are indicated or delimited by dashed lines 41 in FIG. 3. It is to be noted that all of the electrodes are of planar configuration and are delimited by the main surfaces of the piezoelectric member so as to avoid electrical short circuiting with the opposed electrodes. Otherwise, the separation gap between the two portions of ground electrode 22 and the intersected area 4 can advantageously have the same width than that formed between two adjacent elementary signal electrodes of the electrode pattern 21 in order to avoid any negative impact on the homogeneity of the array.

In the manufacture thereof, the piezoelectric member 1 has to be turned upside down to allow carrying out of an electrode etching operation on the rear face of the composite. The etching pattern is now rotated of 90 degrees from that of the opposite pattern to provide elementary signal electrodes on the surface of sub-section B and ground electrodes on sub-section A. The basic electrode etching procedure remains unchanged, i.e., is essentially the same, for both faces of the piezoelectric member 1, and, in a preferred embodiment, symmetry is recommended between the front and rear electrodes. Because no grooving is performed on the composite core during the ion etching operation, the piezoelectric member 1 remains unaltered or unchanged with respect to Lamb wave propagation.

Figure 5A:
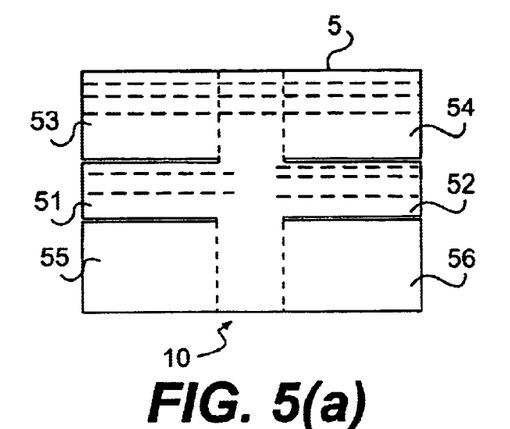
FIG. 5(a) is a top plan view of the device of FIG. 1 with interconnection means positioned thereon in accordance with one step in the assembly of the interconnection means.
Figure 5B:
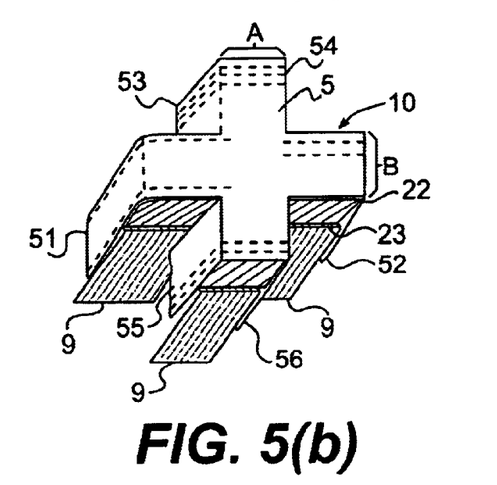
FIG. 5(b) is a perspective view of the device of FIG. 5(a) showing a further step in the assembly of the interconnection means.

The provision of an interconnect means for the crossing array transducer of the invention is something that must be treated with special care so as to provide a fully connected array device without compromising the acoustic performance of the device. A preferred interconnection means arrangement is illustrated in FIGS. 5(a) and 5(b) for a crossed array transducer 10. As shown in FIG. 5(b), the piezoelectric member 1 is sandwiched between front electrode 22 and rear electrode 23. For clarity of illustration, only the signal interconnect means is shown. The necessary connection for the ground electrodes is simply carried out by use of a single tape of copper sheeting, or the like, disposed so as to completely cover the area between the ground electrode and the matching layer (not shown) of the front face. For example, the ground electrode connection means can be advantageously disposed at the corner or edge of the ground electrode in order to not disturb the operation of transducer.

According to the preferred embodiment being considered here, the front and rear interconnection means 5 and 9 are to be distinguished. FIGS. 5(a) and 5(b) better illustrate the front interconnection means 5, and the overall interconnection arrangement for the transducer is further described below. Further, a better understanding of the transducer assembly can perhaps be obtained by considering FIGS. 5(a), 5(b) and 6 together. As shown in FIGS. 5(a) and 5(b), the interconnection circuit 5 is dedicated to connecting transducer elements of the vertical branch. Optionally, the interconnection circuit 5 can have same trace density than that of the array or, more usually, a density of half that density. When half density circuitry is used, the interconnection circuit has to be designed to have even and odd element traces on each side of the circuit as shown in FIG. 5(a). The interconnection circuit 5 can be continuous or discontinuous as illustrated in FIGS. 5(a) and 5(b) without any impact on the manufacturing method or the performance of the transducer. In the case of a continuous interconnection circuit (i.e., a single circuit member or circuit unit), the assembly process is simplified and thus facilitated.

FIGS. 5(a) and 5(b) also illustrate how the interconnection circuit 5 is to be managed in the transducer construction. Alignment between the circuit 5 and the signal electrode of the array is to be carried out in the delimited area where the electrode elements of the transducer are formed. The remaining surface of circuit 5 is split into strips 51, 53, and 55 on one side and strips 52, 54, and 56 on the other side, as shown in FIG. 5(a). A shown in FIG. 5(b), the central strips 51 and 52 are disposed over the surface of lateral branches (as is also evident from FIG. 5(a)) and will extend to the lateral side of the transducer, while the strips 53, 55 and 54, 56 are folded along the lateral faces of the upper and lower portions of the vertical branch.

Figure 6:
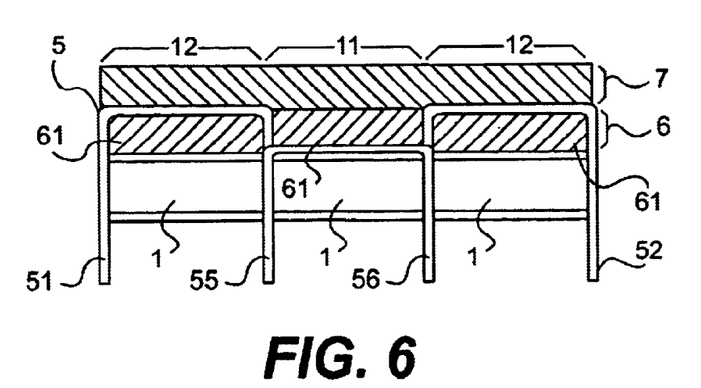
FIG. 6 is a side elevational view, partially in section, of the device of FIG. 1 with a matching layer device, in accordance with a preferred embodiment of the invention, incorporated therein.

FIG. 6 perhaps better illustrates the preferred method for achieving implementation of the interconnection circuit 5 into the transducer assembly. As shown in FIG. 6, circuit 5 passes through the elevation height of the transducer with a change in the vertical level thereof, i.e., is of a special two level configuration as viewed in section in FIG. 6, in order to avoid contact with the ground electrode of the lateral branches. In this regard, in the sectional view shown in FIG. 6, the piezoelectric member 1 is shown as being a combination of a central section 11 and two surrounding sections 12. The central section 11 corresponds to the vertical branch described above at which the elements of the array are to be connected to the circuit 5. Sections 12 represent the two lateral portions of the complementary branch at which the strips 51 and 52 of circuit 5 are disposed.

The circuit 5 is first laminated to the surface of the electrodes of the vertical branch, corresponding to the boundary or delimitation of section 11 in the illustrated embodiment. Next, a first matching layer 6 is assembled to the front face of the transducer. Matching layer 6 is split into a central portion 62 which is defined by the width of the vertical branch and lateral portions 61 corresponding to the ground surface portions of the lateral branch. The matching layer portions 61 and 62 are assembled in such a manner as to sandwich the circuit 5 between their edges, as illustrated. Once the first matching layer 6 is completed, strips 51 and 52 of circuit 5 are folded along the surface of the matching layer portions 61 so as to extend to the outermost lateral faces of transducer, and strips 53, 54, 55, 56 of circuit 5 are folded along the vertical branch as is better shown in FIG. 5(b).

In the next step, a glue or other adhesive material is then provided on the surface of the first matching layer 6 and the interconnection circuits 5 to enable the assembly of second matching layer 7 which covers the entire surface of the transducer. Matching layer 7 also acts as a protective layer for the device, if desired.

The construction described above allows for the use of multiple matching layers, with no limitation as to the number of layers. Further, when the interconnection circuit 5 has a double face or two side metallization pattern, integrated EMI shielding can then be provided for the transducer with essentially no additional effort. Moreover, the interconnecting circuit 5 can easily be integrated into the matching layer member or device (formed, e.g., by matching layers 6 and 7) as an integrated construction, so the assembly of the transducer is even further simplified, and the reliability of the transducer is improved. This method of forming an integrated interconnection circuit/matching layer member enables intermediate acoustic and geometric inspection of the resultant device prior to assembly thereof to the transducer.

According to the acoustic properties of thin circuits such as polyamide (Z=3.2 MRayls), thicknesses below dozen of microns are not actually visible in a transducer pulse response operating in the range of frequencies of 1–12 MHz, when disposed between matching layers or between the piezoelectric member and a matching layer. Even if higher frequency transducer operation is desired in some circumstances, the use of a thinner film of polyamide or liquid resin customized dielectric film is desirable and films are available having thicknesses ranging between 5 to 10 $\mu$m.

With regard to the rear face of the transducer, a similar interconnection operation can be readily carried out. However, because acoustic energy is to be absorbed, or otherwise cancelled, on this side of device, the corresponding face of the piezoelectric member is commonly loaded with an attenuating material or backing member as described above. Therefore, a conventional interconnection method may be more advantageously used here.

Figure 7:
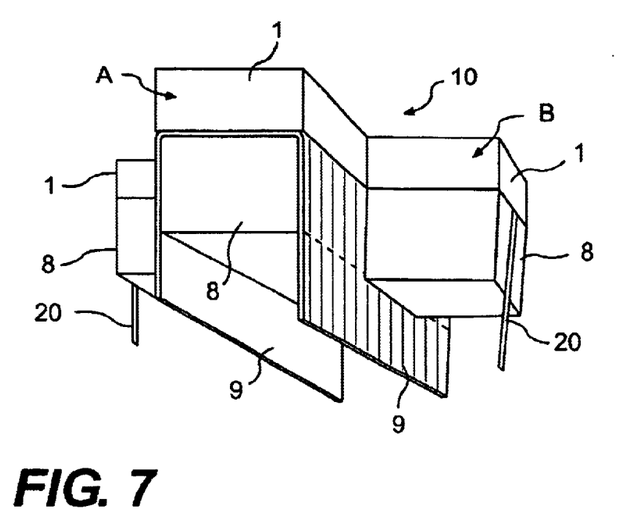
FIG. 7 is a perspective view of the device of FIG. 1 with a backing layer and interconnection means incorporated therewith.

Referring to FIG. 7 where the rear face of the transducer is shown, the piezoelectric member 1 of the transducer 10 is shown with its intersecting branches A and B as in the other figures. The rear interconnection circuit 9 is provided between the elemental electrode pattern (signal electrode) of the piezoelectric member 1 and a backing member 8. The backing member 8 can be made up of a particle-filled molding resin or plastic with acoustic properties in accordance with specified requirements with respect to the required attenuation and mechanical impedance. Assembly of the interconnection circuit 9, the backing member 8 and the piezoelectric member 1 is preferably carried out using a pressure bonding method employing a liquid glue or epoxy. A portion of backing 8 which covers the lateral branch is directly disposed against the surface of one (ground) electrode of the piezoelectric member 1 thereby sandwiching a conductive strip or sheet for making contact with the ground electrode. In general, the interconnection operation at the rear face of the transducer 10 is much easier than that at the front face and inherently it requires no special care or skill to achieve an appropriate interconnection. Downwardly depending metallic strips 20 are connected to the ground electrode of branch B.

Because the transducer assembly forms a sandwich of uniform thickness, the transducer device 10 can be bent or curved into practically any shape as discussed below in connection with FIGS. 9(a) to 9(e). The operations to be performed in bending the surface of transducer are governed by those associated with a thermal forming process. In this process, a planar device and its conformal tool (not shown) are heated to a required temperature (which may be higher than 45° C.), and the device is next positioned on the conformal tool. Pressure is uniformly applied for a preselected period of time, with the temperature thereafter settling down to ambient and the pressure being progressively released. The transducer device so formed will keep its shape as long as no releasing operation occurs (i.e., so long as the device is not exposed to excessive temperatures, etc). Accordingly, the composite intersecting array transducer of the present invention provides expanded possibilities with respect to forming or shaping thereof, in addition to the advantages discussed above with respect to simplicity of manufacture and preservation of acoustic performance.

Upon the completion of transducer assembly, the overlapped elements of the intersected array transducers are connected to a switch or switching device (not shown in FIG. 7 but denoted 12 in FIG. 8), the latter being preferably located in the vicinity of the transducer in order to provide an integrated switching capability for the transducer. More particularly, the signal electrodes of the intersected area 4 (FIG. 3) of the branch A (see, e.g., FIG. 5(b)) extend through the strips 51 and 52 to the switching device. In parallel, the signal electrodes from branch B (FIG. 7) are also connected to the same switching device 12 shown in FIG. 8.

Figure 8:
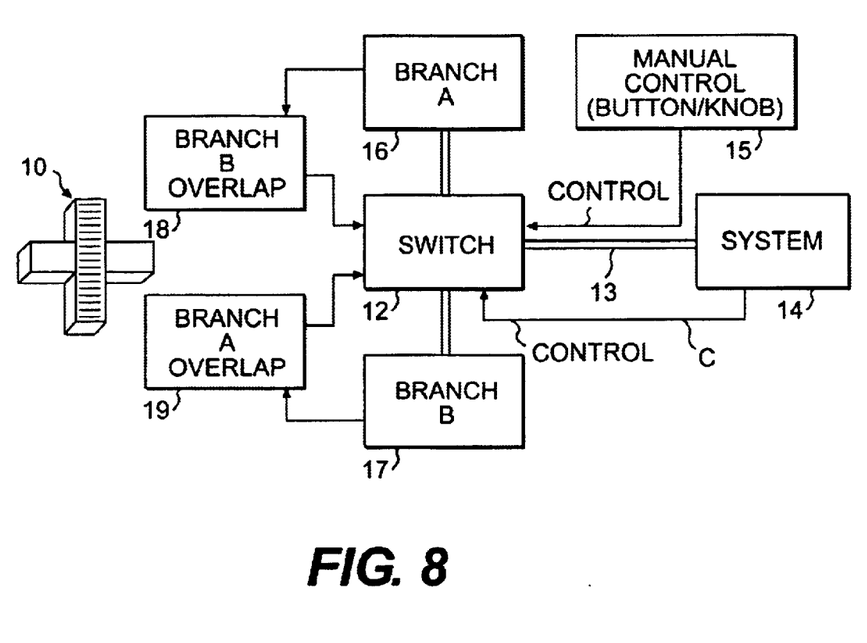
FIG. 8 is a block diagram of the switching and control system for the device of FIG. 1.
Figure 9A:
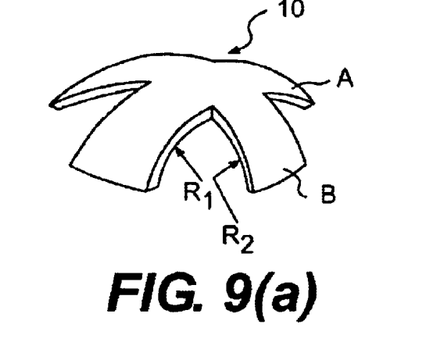
FIGS. 9(a) to 9(e) are perspective views of five different embodiments of the device of FIG. 1 wherein at least two branches thereof are of a curved configuration.
Figure 9B:
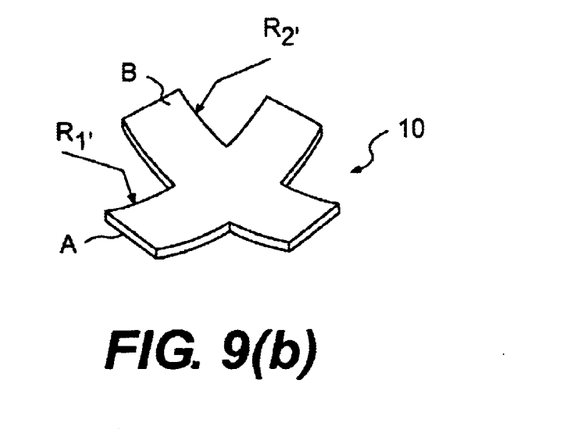
Figure 9C:
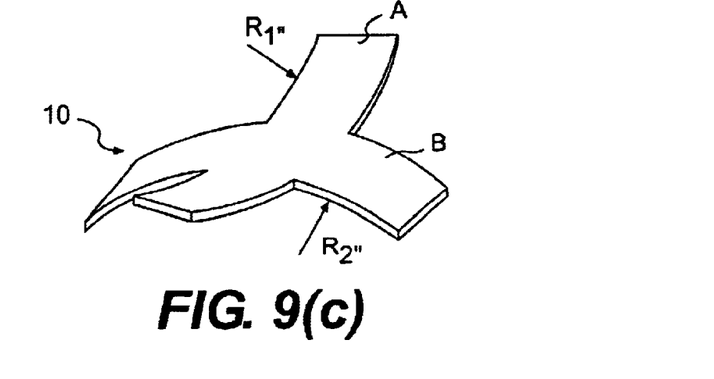
Figure 9D:
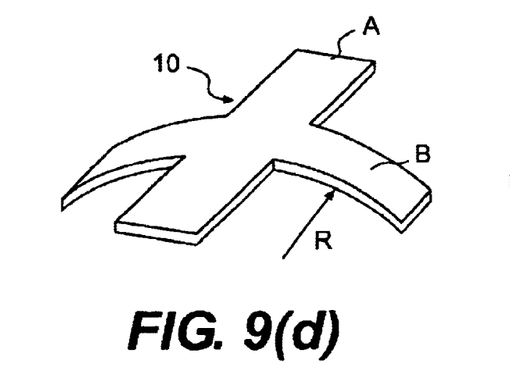
Figure 9E:
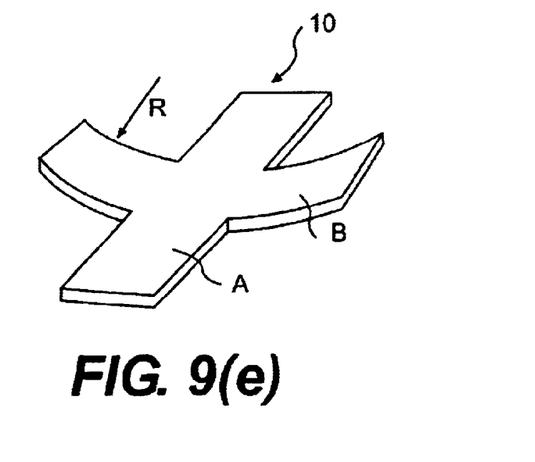

Referring to FIG. 8, wherein a block circuit diagram of the transducer is provided, the switching and multiplexing device 12 is shown centrally of FIG. 8. Switching device 12 can comprise electromechanical switches or semiconductor switches such as those manufactured by Supertex US HV232FG, HV209, HV20822 etc. or Mems switches such as those manufactured by Microswitches, USA.

The outputs of the elements of the array transducers from branches A and B are designated 16 and 17 in FIG. 8 and, with the exception of those of the overlapping or intersected area 4, are routed through the switching and multiplexing device 12 and toward the overall system 14 through an output coaxial cable 13. On the other hand, the outputs of the elements of the overlapping portions indicated at 18 and 19, are managed by the switching device 12 before being fed to the output coaxial cable 13 with transmitted signals from branches 16 and 17.

The switch or switching device 12 can be either controlled manually by push button or knob, indicated at 15, or remote controlled by the system 14 via a wire connection C or a wireless emitter/receiver (not shown). If necessary, a power supply voltage (not shown) can also be provided by the system 14 to switching device 12.

Because the commuting time constant is not as short as that required for a typical beam formation process, a large variety of switches and control devices can be used to implement this aspect of the invention. However, the use of semiconductor multiplexing devices, such as those mentioned above which are obtainable from Supertex, might cause significant heating of the ultrasonic probe. This can be compensated for by the incorporation of heat sinks. On the other hand, mechanical switches or Mems switches are low energy consumption devices and, therefore, present much less risk of heating. Shortcomings, however, still remain such as the audible noise associated with mechanical switches and the higher cost of specific Mems. On the other hand, given the important breakthroughs and technical efforts observed with nanotechnologies and $\mu$-machining methods, the current trends in micro-technology would lead one to expect that Mems devices will shortly replace mechanical switches and partially replace semiconductor multiplexers in this field.

Referring to FIGS. 9(*a*) to 9(*e*) there are shown different configurations of the intersecting array transducer 10 described above. Specifically, a convex shaped intersecting array device 10 is illustrated in FIG. 9(*a*) wherein the first branch A is provided with first radius of curvature R1 and the second, intersecting branch B is provided with second, radius of curvature R2. The R1 and R2 curvatures can be made to be equal in a manner so as to provide spherical convex array transducer.

Similarly to the above, FIG. 9(*b*) represents a concave shaped transducer 10 having a first branch A with a first radius of curvature R1' and a second branch with a second radius of curvature R2'. Again, the curvatures R1' and R2' can be made equal so as to form a spherical concave array transducer device as shown.

In FIG. 9(*c*), there is illustrated a transducer array 10' wherein a first branch A has a positive radius of curvature R1" and the second branch B intersecting the first branch A has a negative radius of curvature R2" which is the opposite of the first, positive radius of curvature R1". In this case, the convex array might be used for imaging scanning while the concave array operates as a treatment device wherein the concave curvature thereof will enhance focusing of the ultrasonic power.

FIGS. 9(*d*) and 9(*e*) show configurations which are quite similar in functionality. In these embodiments, a flat linear branch A of the transducer array device 10 is intersected with a curved array B having a radius of curvature R. In the case where R is positive (FIG. 9(*d*), the transducer device 10 is quite suitable for mounting into an endocavity probe. In this application, the linear branch A is mounted along the azimuth axis of the probe case (not shown) and the curved array B will fit the radius of curvature of the tubular portion of the probe. Both arrays A and B can be used for imaging and the combination of arrays A and B will enable an advanced diagnosis and/or a 3D reconstruction. The transducer device 10 illustrated in FIG. 9(*e*) comprises a first linear branch A intersecting a second curved branch B. The curvature of the curved branch B is negative (i.e., concave) thereby making branch B well adapted for high intensity focused ultrasound (HIFU) use.

Figure 10A:
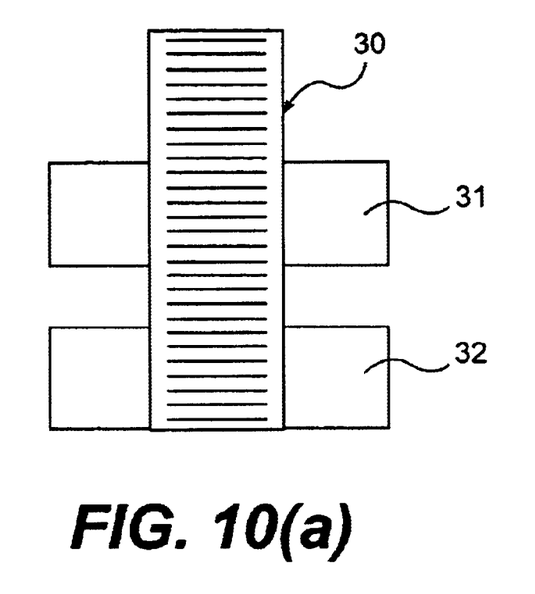
FIGS. 10(a) and 10(b) are plan views of further embodiments of the invention.
Figure 10B:
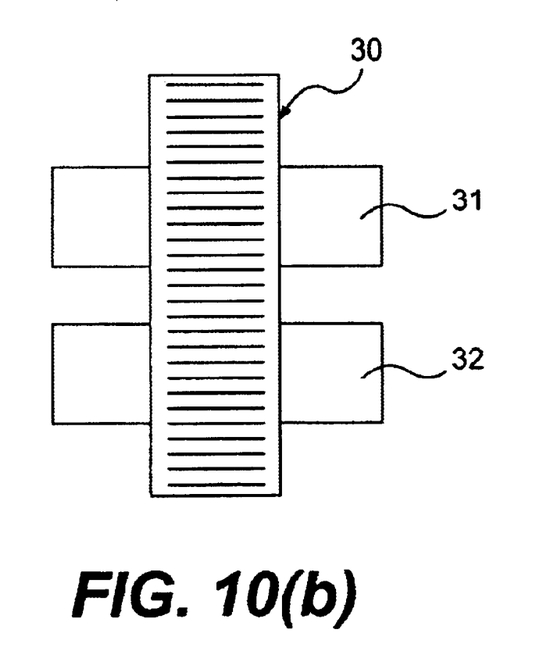

Finally, referring to FIGS. 10(*a*) and 10(*b*), there are shown further variants of an intersecting array transducer according to the invention wherein two (and there could be more) branches extend laterally outwardly from both sides of a primary linear portion. More specifically, in FIG. 10(*a*), a first linear branch 30 is provided (which extends vertically as shown) having the elements thereof arranged along an azimuth axis. A first intersecting branch 31 extends laterally with respect to the first linear branch 30 to form a first crossing area. As above, the electrode patterning of the first intersecting array defined by branch 31 is reversed as compared to that of the first linear branch 30. Preferably, as illustrated, the first intersecting branch extends perpendicularly to, i.e., perpendicularly intersects, the first linear branch 30. At least a second intersecting branch 32 extends laterally of linear branch 30, at one extremity of the linear branch 30 of the transducer. The second intersecting branch 32 preferably extends perpendicularly to the first linear branch 30 to form a second crossing area located at the one extremity of the first linear branch 30. In FIG. 10(*b*), a similar arrangement of intersecting branches is provided except that the positions of intersecting branches 31 and 32 are different, and, in this implementation, branches 31 and 32 are positioned at the middle portion of the linear branch 30. It will be noted that branches 31 and 32 are not necessarily identical to one another and each of the branches 31 and 32 can be constructed so as to provide either imaging acquisition or high intensity ultrasound transmission with no impact on the basic invention.

Although the invention has been described above in relation to preferred embodiments thereof, it will be understood by those skilled in the art that variations and modifications can be effected in these preferred embodiments without departing from the scope and spirit of the invention.

What is claimed:

1. An ultrasonic array transducer, said transducer having a central region and front and rear faces, and comprising:

a first linear array extending through the central region of the transducer and including signal electrodes on the front face of the transducer and ground electrodes on the rear face of the transducer;

a second linear array extending through the central region of the transducer mutually orthogonally to said first linear array, said second linear array including signal electrodes on the rear face of the transducer and ground electrodes on the front face of the transducer;

said first and second linear arrays intersecting to form a cross shaped configuration including a central area at which said first and second arrays intersect, said central area including a central group of signal electrodes from the first array on the front face of the transducer and a central group of signal electrodes from the second array on the rear face of the transducer;

a first interconnection means disposed at the first face of the transducer for providing electrical connection of the signal electrodes of the first array without shunting the ground electrodes of the second array;

a second interconnection means disposed at the rear face of the transducer for providing electrical connection of the signal electrodes of the second array; and a switching device, disposed in the vicinity of the first and second arrays between said first and second interconnection means and external coaxial cables, for switching the central groups of signal electrodes of the first and second arrays between ground and excitation circuitry for providing excitation of the respective central groups, said transducer further comprising a further linear array interecting said first linear array, and said further linear array including signal electrodes on the rear face of the transducer, and ground electrodes on the front face of the transducer.

2. A transducer according to claim 1 wherein said first linear array constitutes means for carrying out an imaging operation and the second linear array constitutes means for providing patient therapy.

3. An ultrasonic intersecting array transducer according to claim 1 wherein said second linear array has a resonant frequency substantially lower than that of the said first linear array.

4. An ultrasonic intersecting array transducer according to claim 1 wherein said second linear array comprises an elemental electrode arrangement different than that of said first linear array.

5. An ultrasonic intersecting array transducer according to claim 1 wherein the transducer is curved and forms a sector shaped probe.

6. An ultrasonic intersecting array transducer according to claim 1 wherein the first linear array is curved and has a first radius of curvature and the second linear array is curved and has a second radius of curvature.

7. An ultrasonic intersecting array transducer according to claim 1 wherein the transducer is convex shaped.

8. An ultrasonic intersecting array transducer according to claim 1 wherein the transducer is concave shaped.

* * * * *